United States Patent [19]

Mikalov et al.

[11] Patent Number: 5,078,743
[45] Date of Patent: Jan. 7, 1992

[54] METHOD OF PLACING AN ESOPHAGEAL VOICE PROSTHESIS IN A LARYNGECTOMIZED PERSON

[76] Inventors: Abraham Mikalov, 5700 Collins Ave., Apt. 8-H, Miami Beach, Fla. 33141; Jamie S. Barkin, 9640 W. Broadview Dr., Bay Harbor, Fla. 33154

[21] Appl. No.: 511,484

[22] Filed: Apr. 19, 1990

[51] Int. Cl.⁵ .............................................. A61F 2/20
[52] U.S. Cl. ........................................ 623/9; 623/11; 606/108; 128/898; 604/164
[58] Field of Search ..................... 606/108; 128/898; 623/9, 11; 604/164

[56] References Cited

U.S. PATENT DOCUMENTS

| | | | |
|---|---|---|---|
| 4,614,516 | 9/1986 | Blom et al. | 623/9 |
| 4,808,183 | 2/1989 | Panje | 623/9 |
| 4,826,481 | 5/1989 | Sacks et al. | 604/164 |
| 4,911,716 | 3/1990 | Blom et al. | 623/9 |

OTHER PUBLICATIONS

Mark Singer and Eric Blom—"An Endoscopic Technique for Restoration of Voice After Laryngectomy—Annals of Otology, Rhinology and Laryngology"-Nov. Dec.-1980 vol. 89, No. 6 pp. 529–533.

*Primary Examiner*—Stephen C. Pellegrino
*Assistant Examiner*—Glenn K. Dawson
*Attorney, Agent, or Firm*—Caesar, Rivise, Bernstein, Cohen and Pokotilow, Ltd.

[57] ABSTRACT

A method of placing an esophageal voice prosthesis in a patient who has undergone a laryngectomy to be performed by a surgeon to permit the patient to restore speech patterns. The method comprises the steps of sedating the patient under local anesthesia, introducing a flexible endoscope into the patient's mouth so that it reaches the patient's esophagus, introducing a Seldinger needle into the patient to puncture the tracheostoma and enter the esophagus and create a passageway therethrough. The surgeon measures the tracheostoma length to determine the proper sized prosthesis to use by threading a measuring catheter and length of gastrostomy tubing about a guide wire to the prosthesis implantment site. The measuring catheter is removed with the guide wire in place, and a voice prosthesis is attached to the gastronomy tubing and threaded over the guide wire so that the prosthesis is in place at the implantment site. The gastronomy tubing is then removed and the prosthesis is ready for use.

4 Claims, 6 Drawing Sheets

METHOD OF PLACING AN ESOPHAGEAL VOICE PROSTHESIS IN A LARYNGECTOMIZED PERSON

BACKGROUND OF THE INVENTION

This invention relates generally to voice prostheses and implantation procedures, and more specifically to a Method of Placing An Esophageal Voice Prosthesis In A Laryngectomized Person, to be performed by a surgeon on a patient who has undergone a laryngectomy (removal of the voice box) due to cancer or other conditions.

Advanced laryngeal carcinoma and its treatment have devastating effects on speech, swallowing, and respiration, and pose numerous challenges to a clinician. The impact of speech loss (aphonia) on the quality of life has few equals among medical handicaps. Speech provides an individual's presentation to society as well as his or her self-perception. Aphonia not only disrupts commerce with others but also changes relationships and dependencies, which may produce serious psychological stress and behavioral alterations. An individual's failure to adjust to this problem frequently results in permanent disability and withdrawal from society, sometimes leading to suicide.

Voice preservation has been an inseparable concern from the effective therapy of laryngeal cancer, as seen in the evolution of treatment over nearly 100 years. Rehabilitation of the voice may consist of an artificial larynx, acquisition of an esophageal voice, or a second operative procedure to restore continuity of the airway and alimentary tract. In addition, surgeons have developed neoglottic reconstructive procedures for total or near-total laryngectomy to diminish delays in secondary voice rehabilitation. A historical review of such treatments and devices may be found in Vocal Rehabilitation With Prosthetic Devices, Surgery For Cancer Of The Larynx, Drs. M. Singer, E. Blom.

A vocal rehabilitative method must be capable of solving a number of critical problems. Rehabilitation must not limit adequate cancer treatment in terms of the extent of surgical resection or tolerance to conventional-dose radiation therapy. Resulting deglutition should be normal and rapidly reacquired postoperatively. Patients should be free of dependence on complicated valves, tubes, and external devices; frequent endoscopy, dilatations, and revisions should not be required, oftentimes required by the prior art methods and devices. Prior art devices and methods have therefore suffered numerous drawbacks.

For example, the technique of developing esophageal speech patterns requires that the patient's main tracheal airway be connected to the central lower portion of the neck (tracheostoma). Swallowing occurs in the normal fashion through the hole in the neck after a laryngectomy. Esophageal speech is a technique which the patent can master without additional surgery or mechanical devices and is equivalent to a "belch." The patient belches air from the stomach into the posterior wall of the upper esophagus to create vibratory sounds in the back of the throat mimicking speech. This technique however suffers from the drawback that the patient can say only one or two words with each belch.

Devices such as the battery-powered electro-larynx devices available from Bell Laboratories have been frequently used to assist a patient in producing speech. This hand-held device is held against the side of the neck as the patient mimics words with his mouth, so that the device generates comprehensible vibratory sounds. This device does not require any surgery for use, however, many patients cannot master the technique to produce speech and others are extremely unhappy with the quality of the sound produced.

The VoiceBak artificial larynx developed by Dr. Taub in 1972, utilized an external shunt and required construction of a secondary esophagostoma in the lower lateral neck. This external device was inserted by attaching it at the esophagostoma, using a trumpet-shaped silicone connector, and tightening it against the skin with an adjustable tension collar. Tubing then traveled to a one-way saliva valve and to a regulator valve worn on the upper chest. This valve mechanism allowed two-way airflows for normal respiratory exchange. This device suffered from numerous drawbacks, including difficulty installing and maintaining the relatively large external device and the requirement of an additional esophagostoma.

Another prior method of voice restoration is commonly known as the trachea esophageal puncture method. Devices utilizing this method route air from the lungs directly into the esophagus through a tracheal esophageal puncture which is a hole made directly in the tracheostoma into the esophagus which lies directly behind it. A device such as a one-way valve is then inserted to vent air forced up through the trachea and directly into the esophagus. This permits a greater volume of air to enter the esophagus and create a vibratory sense similar to the sound developed with a belch. However, due to the increased volume, the patient may speak for a longer period of time and with more audible speech. One such device is that developed by Drs. Blom and Singer, known as the BLOM-SINGER Low Pressure Voice Prosthesis, covered by U.S. Pat. No. 4,614,516, manufactured and distributed by the American V. Mueller Co., a division of Travenol Labs, Inc., Anasco, Puerto Rico 00610.

The current method for the placement of this device requires that the patient be under general anesthesia. A rigid endoscope is introduced through the mouth and into the esophagus to aid the physician in puncturing the tracheostoma from outside. A rubber catheter is introduced through the tracheoesophageal fistula and must remain in place for 72 hours to permit the wound to heal before the duck-bill prosthesis is placed into the fistula. This prosthesis is a one-way valve which allows air to be vented directly from the trachea and into the esophagus.

The current method of placing this device in the operative position however, suffer from numerous drawbacks and complications. For example, the patient must undergo general anesthesia and suffer the inherent life-threatening risks associated therewith. Additionally, the rigid endoscope often traumatizes the esophagus and may cause a leak into the chest cavity (mediastinitis), which results in discomfort to the patient and a prolonged recovery period.

The method of the present invention overcomes the disadvantages of the prior art by providing a simple, safe and easily accomplished technique to place in a patient an esophageal voice prosthesis, which will benefit a large number of laryngectomees, without subjecting the patient to general anesthesia or requiring a lengthy hospital stay.

OBJECTS OF THE INVENTION

Accordingly, it is a general object of this invention to provide a safe and easy method of inserting a voice prosthesis in a patient under local anesthesia without requiring lengthy post-operative hospitalization.

It is also an object of this invention to provide a method of inserting a voice prosthesis which can be readily accomplished with the use of a flexible endoscope.

It is a further object of this invention to provide a method of inserting a voice restorative device which can be used immediately after placement in a patient.

It is yet a further object of this invention to provide a method of inserting a voice restorative device which is inexpensive, safe, and presents minimal complications during use.

It is a yet still a further object of this invention to provide a method of speech restoration which is easy to use and permits an individual having undergone a laryngectomy to communicate more effectively by producing speech in a satisfactory quality and quantity, while minimizing effort and discomfort.

SUMMARY OF THE INVENTION

These and other objects of this invention are achieved by providing a method for a surgeon to restore speech in a patient who has undergone a surgical removal of the voice box. The surgeon implants a voice restorative prosthesis in a procedural method comprising the steps of sedating the patient having a tracheostoma under local anesthesia and introducing a flexible endoscope into the patient's mouth until it reaches the patient's esophagus. The surgeon then introduces a Seldinger needle into the patient to puncture the tracheostoma and esophagus and create a passageway therethrough. The surgeon then visualizes the introduction of the Seldinger needle through the flexible endoscope.

The next step is to insert and thread a guide wire through the outer cannula of the Seldinger needle directly into the patient's esophagus and out through the patient's mouth and remove the outer cannula. The surgeon then provides a measuring catheter having a distal end with graduated, pre-measured lines, and a proximal end, and threads the guide wire through the distal end and out through the proximal end of the measuring catheter.

The next step is to guide the measuring catheter directly over the guide wire, and through the patient's mouth and esophagus until the measuring catheter extends through the passageway in a retrograde fashion, so that the proximal end abuts the esophagus at the site of the passageway. At this point, the surgeon can see the pre-measured lines extending through and out the passageway, which permits the necessary measurement of the tracheostoma to determine the proper sized prosthesis to use. The measuring catheter is then removed from the patient through the patient's mouth. The voice restorative catheter prosthesis is chosen and releasably connected to a length of gastrostomy tubing to aid in placing the device. The prosthesis and gastrostomy tubing are then threaded over the guide wide through the gastronomy tubing and then through the prosthesis's distal end and out through the proximal end. The prosthesis and gastrostomy tubing are then guided over the guide wire and through the patient's mouth and esophagus until the prosthesis extends through the passageway in a retrograde fashion. The surgeon then severs the length of the tubing extending beyond the patient's neck and removes the guide wire from the patient.

DESCRIPTION OF THE DRAWINGS

Other objects and many attendant features of this invention will become readily appreciated as the same becomes better understood by reference to the following detailed description when considered in connection with the accompanying drawings wherein.

DETAILED DESCRIPTION OF THE PREFERRED EMBODIMENTS

Figure 1:
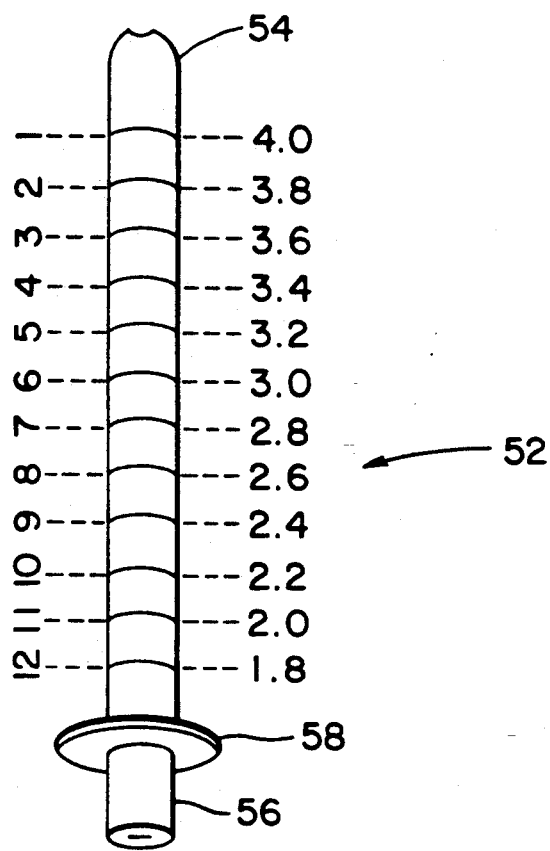
FIG. 1 is an enlarged plan view of the measuring catheter used in the method of the present invention.
Figure 2:
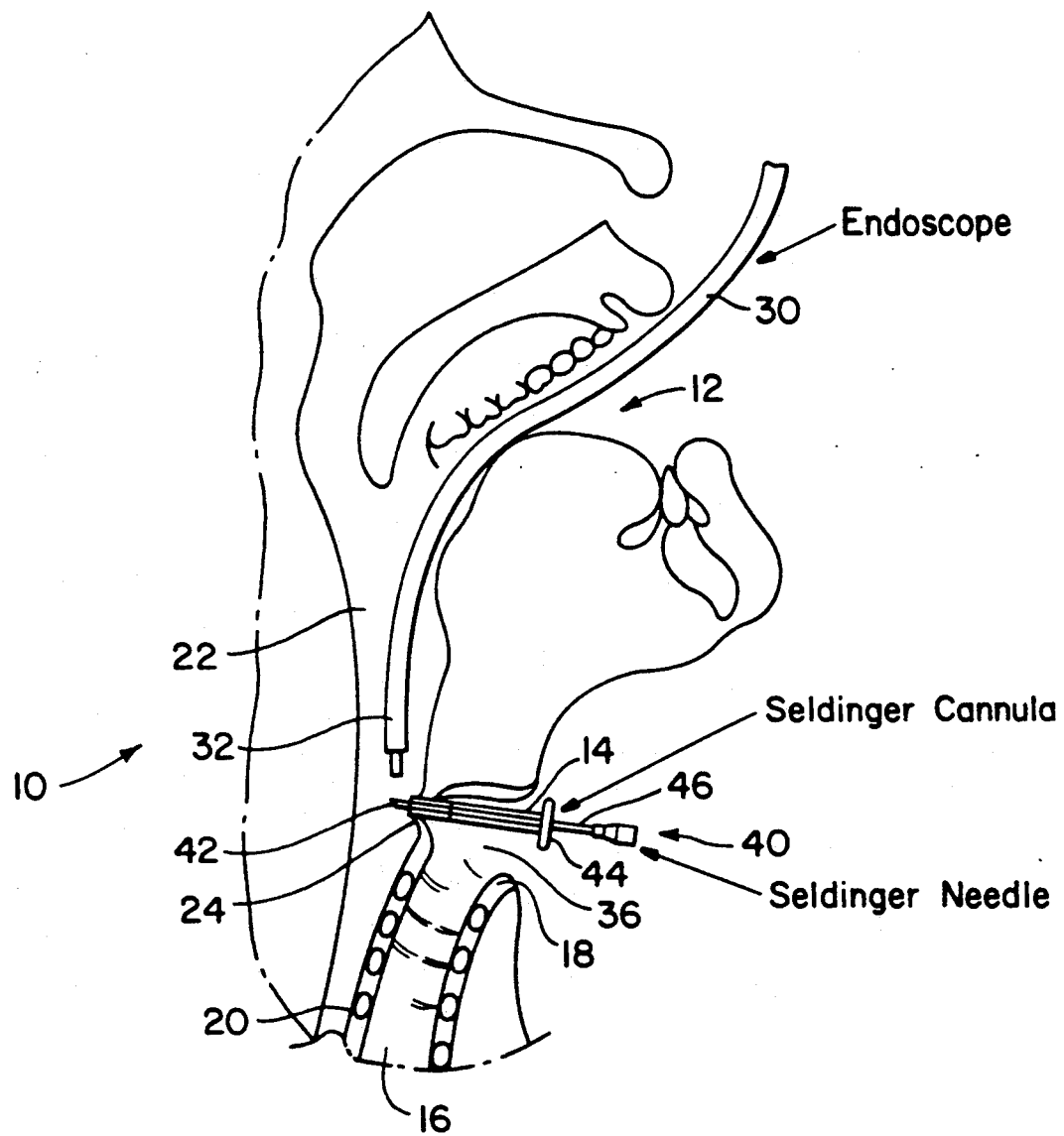
FIG. 2 is an enlarged partial cross-sectional view of a living being with a flexible endoscope and Seldinger needle and catheter in place in accordance with the method of the present invention.

Referring now to various figures of the drawings where like reference numerals refer to like parts there is shown at 10 in FIG. 2 a patient 10 who has undergone a prior laryngectomy. In accordance with the method of the present invention, the surgeon provides the patient 10 with a voice restorative prosthesis 70 as shown in more detail in FIGS. 5 and 6.

The method of the present invention comprises the following steps. First, the patient 10 is sedated with a topical anesthetic at the site where the procedure is to be performed and is given an intravenous sedation with a benzodiazepam compound. Although any suitable medications may be used depending on the circumstances, it is preferable to use a 1% local Xylocaine or Cetacaine topical anesthetic at the operative site and an intravenous solution of approximately 10 milligrams of Valium.

It is preferable to use a local versus general anesthetic to avoid the associated complications and risks associated with general anesthesia. The patients who most often undergo a voice prosthesis implantation are oftentimes at greatest risk in developing complications due to general anesthesia, because of such conditions as advanced age and/or poor general health.

As shown in detail in FIG. 2, the surgeon then uses direct visualization to introduce a flexible fiber optic video upper endoscope 30 into the patient's mouth 12 and through the esophagus 22, so the endoscope 30 is at the operative site near the tracheostoma 14. The endoscope 30 enables the surgeon to view the procedure on a screen (not shown). The endoscope 30 also enables the surgeon to use the device to assist in the various steps in the present method.

After endoscopic visual inspection of the laryngectomy site for evidence of any recurrence of cancer or other disease, the endoscope 30 is gently passed through the esophagus 22 and then down into the stomach (not shown) where any remaining gastric contents or secretions are evacuated to reduce the risk of aspiration. The patient 10 is then moved from the standard left lateral (not shown) to decubitus position (not shown) into the supine position (not shown). The endoscope 30 is then withdrawn from the stomach into the proximal esophagus 34 adjacent to the tracheostomy aperture site 36. Air is insufflated through the endoscope 30 to dilate the esophagus 22 and the endoscope tip 32 may be directed against the anterior wall 20 of the esophagus 22 as needed to stabilize and impart some rigidity.

A 14-gauge intravenous angiocatheter stylet, such as the Seldinger needle 40, is directed posteriorly through the superior (12 o'clock) aspect of the mucocutaneous portion (not shown) of the tracheostoma 14 to puncture the anterior esophagus 20 and create a passageway (tracheoesophageal fistula) 24 through the trachea 16 and the esophagus 22. Once the passageway 24 is created, the outer cannula 44 of the Seldinger needle 40 remains in the passageway 244 while the central needle 46 is removed. The surgeon may visualize the introduction of the Seldinger needle through the aid of a typical flexible endoscope 30 which may utilize conventional fiber optical devices. At this juncture, the endoscope 30 may be removed from the patient 10.

The surgeon then inserts and threads a guide wire 50, through the outer cannula 44 of the Seldinger needle directly into the patient's esophagus 22 and out through the patient's mouth 12. Preferably the guide wire 50 is a 0.025 cm biliary guide wire, although any suitably sized guide wire may also be used.

Figure 3:
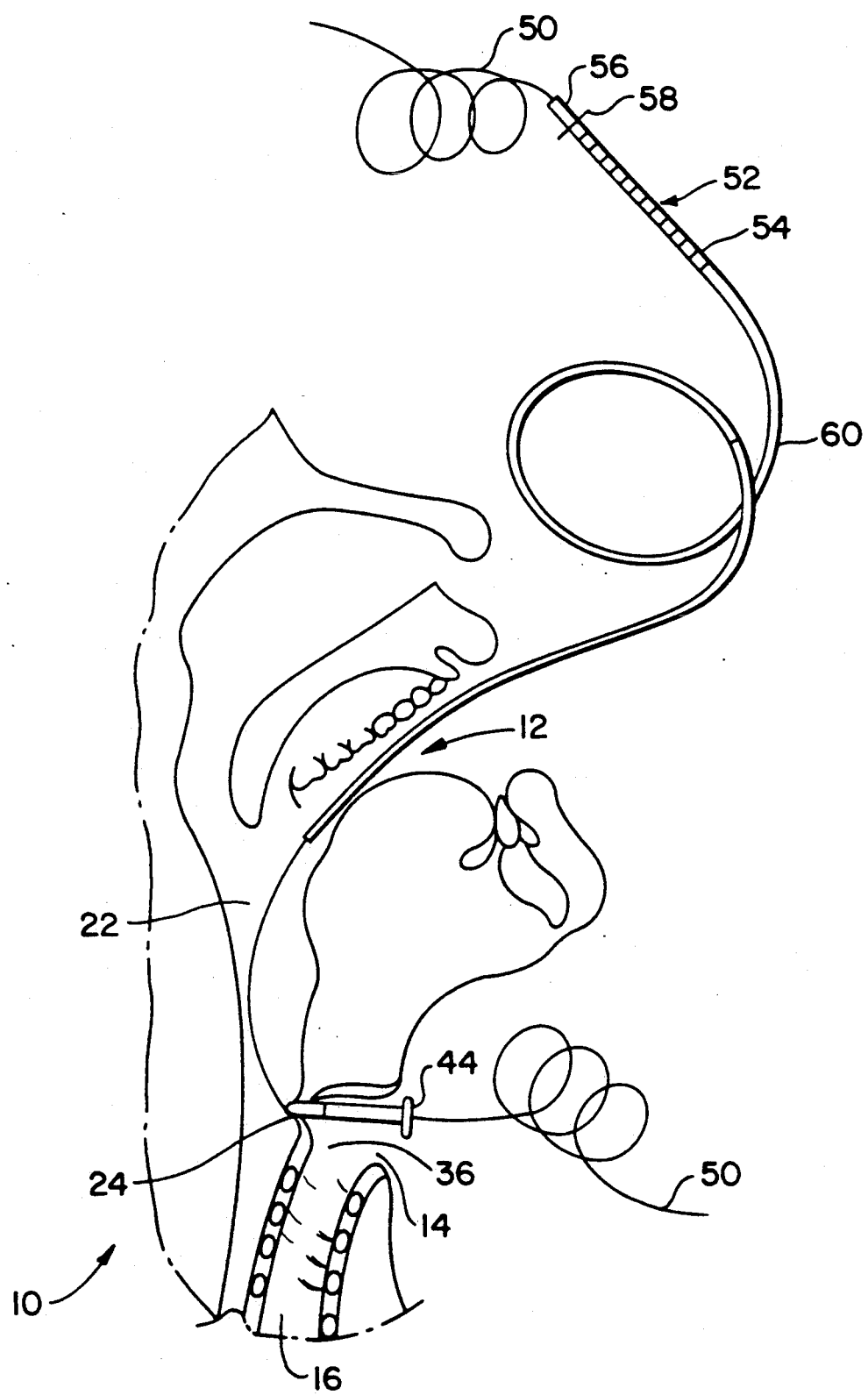
FIG. 3. is an enlarged partial cross-sectional view of a living being showing the threading of the measuring catheter and length of gastrostomy tubing along a guide wire in accordance with the method of the present invention.

As shown in FIG. 3, the surgeon then provides a measuring catheter 52 having a distal end 54 with two sets of graduated, pre-measured lines along the catheter's longitudinal axis, and a proximal end 56 having flange 58. The graduated lines provide the surgeon with a means to measure the length of the outer stoma site 14. One set of graduations is numbered 1 through 12, in 1.0 standard intervals in ascending order, beginning from the distal end 54. The second set of graduations is numbered 1.8 through 4.0, in 0.2 cm intervals in ascending order, beginning from the proximal end 56. The surgeon then threads the guide wire 50 through gastronomy tubing 60 and then through the distal end 54 and out through the proximal end 56 of the measuring catheter 52 which is attached to a length of gastrostomy tubing 60 to aid the surgeon in threading the measuring catheter 52 into position. Although the gastrostomy tubing 60 may be made from any suitable material it is preferably made from a resilient material such as SILASTIC.

Figure 4:
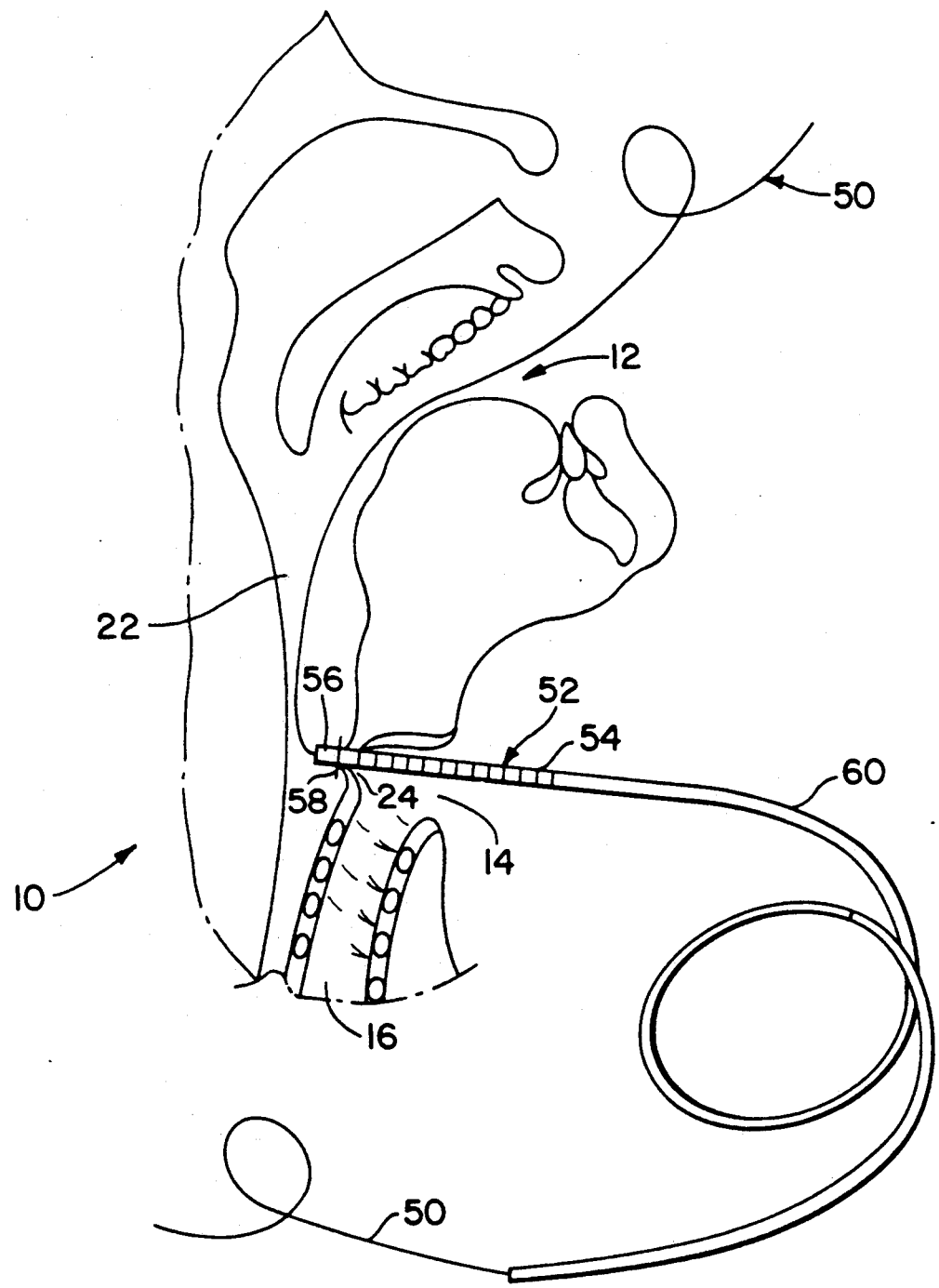
FIG. 4 is an enlarged partial cross-sectional view of a living being with the measuring catheter in place at the esophageal puncture site in accordance with the method of the present invention.

The surgeon then guides the measuring catheter 52 and gastrostomy tubing 60 directly over the guide wire 50, and through the patient's mouth 12 and esophagus 22 as the outer cannula 44 is removed concomitantly or subsequently, so that the measuring catheter 52 extends through the passageway 24 in a retrograde fashion, so that the flange 58 located near the proximal end 56 abuts the esophagus at the site of the passageway (or fistula) 24 as shown more clearly in FIG. 4. At this point, the surgeon can see the pre-measured lines extending through and out the passageway 24 which permits the necessary measurement of the outer stoma site 14 to determine the proper sized prosthesis to use. The surgeon measures the outer stoma site 14 by noting the proper line on the measuring catheter 52 which coincides with the patient's tracheostoma exit site. The measuring catheter 52 and gastrostomy tubing 60 are then removed from the patient 10 through the patient's mouth 12.

The voice restorative catheter prosthesis 70 is then chosen with a length appropriate for the patient's tracheostoma 14. Although any suitable prosthesis may be used, it is preferable to use the Blom-Singer device previously described. The prosthesis 70, shown more clearly in FIGS. 5 and 6 has a proximal end 72, and a longitudinal axis 76 along which flange 82 is located near the proximal end 72. The prosthesis 70 also has a one-way air valve 78 and retaining flap 80 at its distal end 74. The one-way air valve 78 permits air to flow from the esophagus 22 through the valve and out of the body which enables the patient 10 to speak. Although the prosthesis 70 may be comprised of any suitable material, it is preferable that it be made from a radiopaque type material such as SILASTIC.

Figure 5:
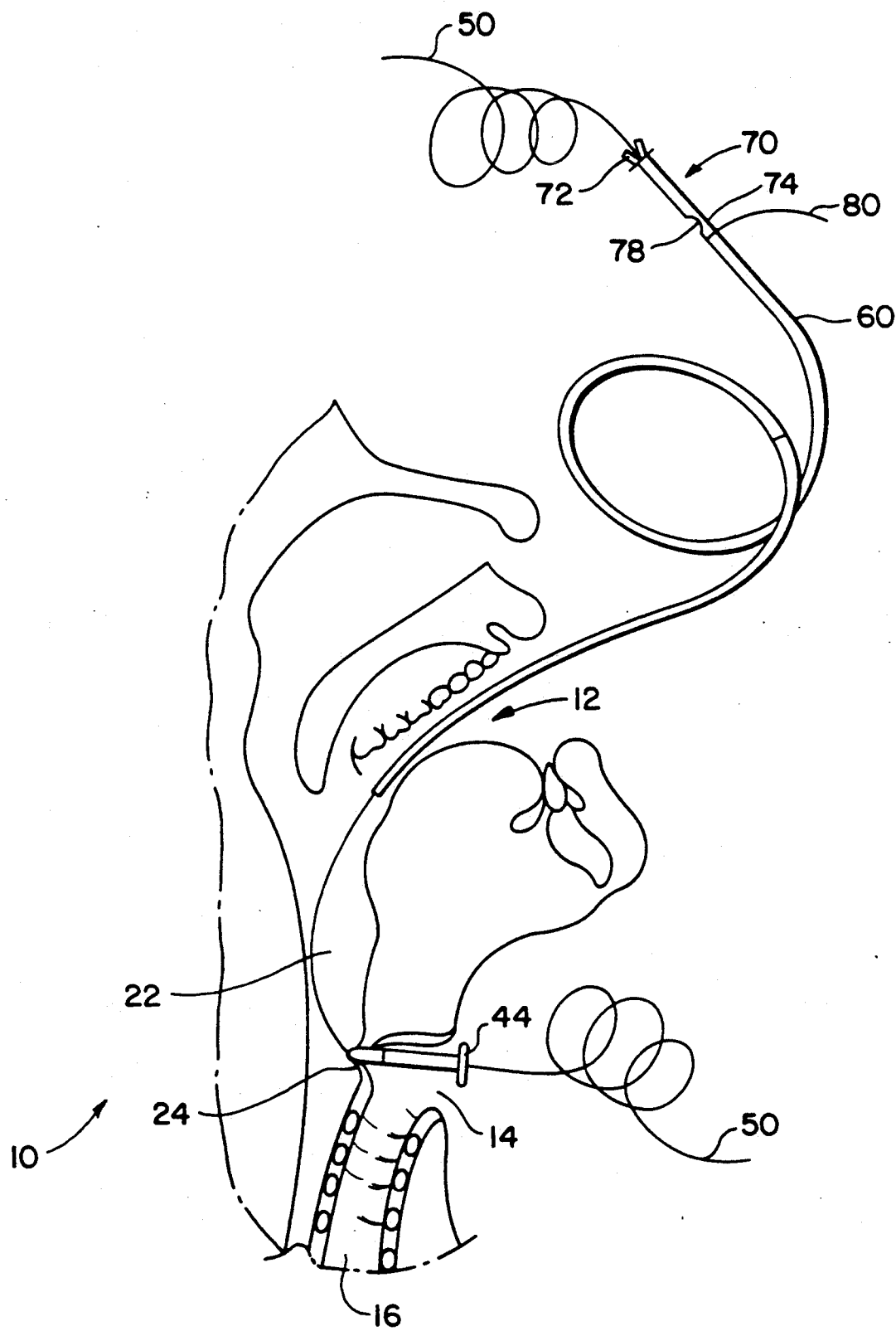
FIG. 5 is an enlarged partial cross-sectional view of a living being showing the threading of the voice restorative prosthesis and gastrostomy tubing along a guide wire in accordance with the method of the present invention.
Figure 6:
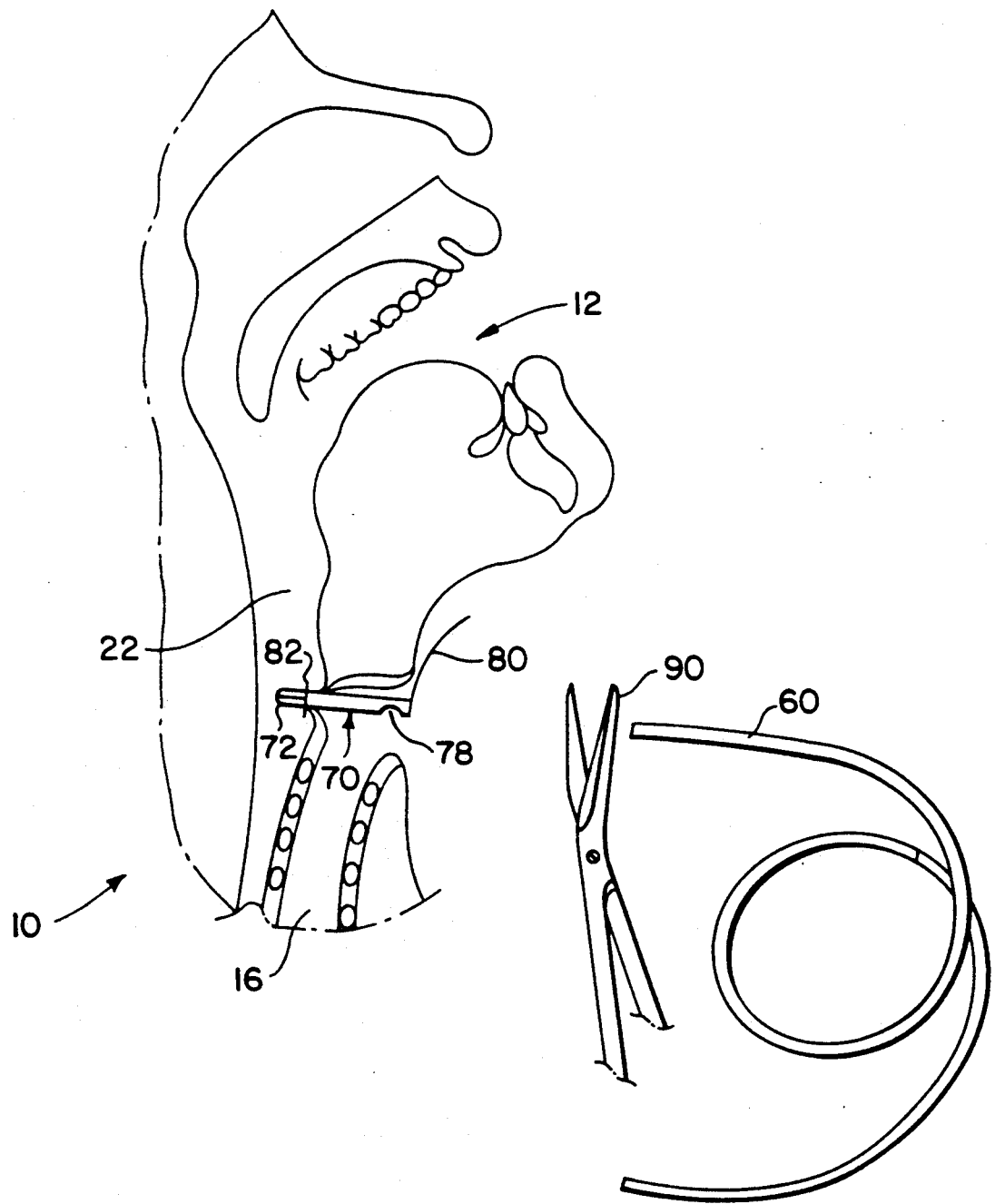
FIG. 6 is an enlarged partial cross-sectional view of a living being with the voice restorative prosthesis in the operative position in accordance with the method of the present invention.

As shown more clearly in FIG. 5, the distal end 74 of prosthesis 70 is attached to a piece of gastrostomy tubing 60 and both are then threaded over the guide wide 50 through the distal end 74 and out through the proximal end 72. The prosthesis 70 and tubing 60 then pass through the patient's mouth 12 and esophagus 22 until the prosthesis 70 extends through the passageway 24 in a retrograde fashion so that the flange 82 abuts the anterior esophagus 20. As shown in FIG. 6, the surgeon may then sever the gastrostomy tubing 60 connected to the prosthesis 70 with any suitable cutting means, such as a pair of conventional surgical scissors 90. The retaining flap 80 is then secured to the skin of the patient with adhesive tape (not shown) or any other suitable adhesive, to prevent aspiration of the device. The prosthesis 70 is then ready to be used by the person to produce speech.

Without further elaboration the foregoing will so fully illustrate our invention that others may, by applying current or future knowledge, readily adapt the same for use under various conditions of service.

We claim:

1. A method of restoring speech in a patient who has undergone a surgical removal of the voice box to be performed by a surgeon or other person to provide the patient with a voice restorative prosthesis, said patient having a esophagus, mouth and tracheostoma, said method comprising the steps of:
   a. sedating said patient under local anesthesia;
   b. providing a flexible endoscope and introducing said flexible endoscope into the patient's mouth until the flexible endoscope reaches the patient's esophagus;
   c. providing a Seldinger needle having an outer cannula and introducing said Seldinger needle into the patient so that the Seldinger needle punctures the tracheostoma and enters said patient's esophagus to create a passageway therethrough, while the surgeon visualizes the introduction of the Seldinger needle through the flexible endoscope;
   d. providing a guide wire and threading said guide wire through the outer canula of the Seldinger needle directly into the patient's esophagus and out through the patient's mouth;
   e. providing a measuring catheter having a distal end with graduated, pre-measured lines, and a proximal end, and threading said guide wire through said distal end and out through said proximal end of the measuring catheter;

f. guiding the measuring catheter directly over the guide wire, and through patient's mouth and esophagus until the measuring catheter extends through said passageway in a retrograde fashion so that said proximal end abuts said esophagus at the site of the passageway and the surgeon can see the pre-measured lines extending through and out said passageway;

g. measuring the length of the tracheostoma using the measuring catheter;

h. removing the measuring catheter from the patient through the patient's mouth;

i. providing a length of catheter tubing having a voice restorative prosthesis attached to the catheter tubing, said voice restorative prosthesis having a length appropriate for the patient's tracheostoma, a distal end having a one-way valve and a flexible retaining flap, and a proximal end having a flange;

j. threading said guide wire through said catheter tubing and through the distal end of the prosthesis and out through said proximal end of said prosthesis;

k. guiding said catheter tubing and said prosthesis directly over the guide wire through the patient's mouth and esophagus until the prosthesis extends through said passageway in a retrograde fashion so that the flange abuts the anterior of the patient's esophagus and the flexible retaining flap is located outside of the patient; and l. severing said distal end of said catheter tubing.

2. The method of claim 1 additionally comprising the step of:

a. advancing said flexible endoscope to the patient's stomach to remove any contents therein and withdrawing the flexible endoscope to the tracheostoma prior to providing the Seldinger needle.

3. The method of claim 1 additionally comprising the step of removing said flexible endoscope from said patient prior to providing said measuring catheter.

4. The method of claim 1 wherein the step of sedating said patient under local anesthesia additionally comprises the steps of:

a. providing a 1% Xylocaine or Cetacaine topical anesthetic to said patient and administering the topical anesthetic at the tracheostoma and surrounding areas; and b. providing an intravenous solution of approximately 10 milligrams of Valium administering the intravenous solution to the patient.

* * * * *